(12) United States Patent
Schöpf et al.

(10) Patent No.: US 6,988,015 B1
(45) Date of Patent: Jan. 17, 2006

(54) BONE IMPLANT

(75) Inventors: Christoph Schöpf, Möhrendorf (DE);
Karl Koschatzky, Erlangen (DE);
Rolf-Dieter Kalas, Söhrewald 1 (DE);
Matthias Löwel, Nürnberg (DE)

(73) Assignee: Tutogen Medical GmbH, Neunkirchen am Brand (DE)

(*) Notice: Subject to any disclaimer, the term of this patent is extended or adjusted under 35 U.S.C. 154(b) by 390 days.

(21) Appl. No.: 10/129,348

(22) PCT Filed: Oct. 30, 2000

(86) PCT No.: PCT/EP00/10673

§ 371 (c)(1),
(2), (4) Date: Jul. 10, 2002

(87) PCT Pub. No.: WO01/32107

PCT Pub. Date: May 10, 2001

(30) Foreign Application Priority Data

Nov. 2, 1999 (DE) ................ 199 52 550

(51) Int. Cl.
A61F 2/02 (2006.01)
G06F 19/00 (2006.01)

(52) U.S. Cl. ................ 700/98; 623/16.11
(58) Field of Classification Search ......... 700/95–98, 700/117–120, 159–161, 182, 197; 623/16.11, 623/18.11, 23.63, 901
See application file for complete search history.

(56) References Cited

U.S. PATENT DOCUMENTS

| 4,436,684 A |   | 3/1984 | White ............... 264/138 |
| 4,627,853 A | * | 12/1986 | Campbell et al. ....... 128/898 |
| 4,976,737 A | * | 12/1990 | Leake ................ 128/898 |
| 5,139,527 A | * | 8/1992 | Redl et al. ............ 623/66.1 |
| 5,156,777 A |   | 10/1992 | Kaye ................ 264/40.1 |
| 5,452,407 A | * | 9/1995 | Crook ............... 345/421 |
| 5,735,277 A | * | 4/1998 | Schuster ............. 600/425 |
| 5,741,215 A | * | 4/1998 | D'Urso ............. 600/407 |
| 5,899,939 A | * | 5/1999 | Boyce et al. ........ 623/16.11 |
| 6,112,109 A | * | 8/2000 | D'Urso ............. 600/407 |
| 6,118,043 A | * | 9/2000 | Nies et al. .......... 623/23.56 |
| 6,254,639 B1 | * | 7/2001 | Peckitt ............. 623/11.11 |
| 6,413,089 B1 | * | 7/2002 | Ashman et al. ........ 433/174 |
| 6,506,217 B1 | * | 1/2003 | Arnett ............. 623/23.61 |
| 6,605,117 B2 | * | 8/2003 | Kuberasampath et al. ........ 623/23.58 |
| 6,719,793 B2 | * | 4/2004 | McGee ............. 623/16.11 |

FOREIGN PATENT DOCUMENTS

| DE | 73 41 222 U1 | 2/1974 |
| DE | 29 06 650 C2 | 8/1980 |
| DE | 32 05 526 C2 | 9/1983 |
| DE | 35 22 196 A1 | 2/1986 |
| DE | 36 26 549 A1 | 2/1988 |
| DE | 38 04 310 C2 | 7/1989 |
| DE | 88 08 699 U1 | 9/1989 |
| DE | 91 09 121 U1 | 11/1991 |

(Continued)

OTHER PUBLICATIONS

H.H. Lubinus et al. "Ein Pfannenring mit Pfeilerschrauben zur Uberbruckung von Knochendefekten im Acetabulum" Chirurg (1989) 60:819-820, no translation.

(Continued)

Primary Examiner—Maria N. Von Buhr
(74) Attorney, Agent, or Firm—Gifford, Krass, Groh, Sprinkle, Anderson & Citkowski, P.C.

(57) ABSTRACT

The inventive bone implant for replacing defective joint sockets comprises a base body (10) consisting of preserved natural spongiosa with an approximately hemispherical cavity (12).

5 Claims, 2 Drawing Sheets

FOREIGN PATENT DOCUMENTS

Figure 1:
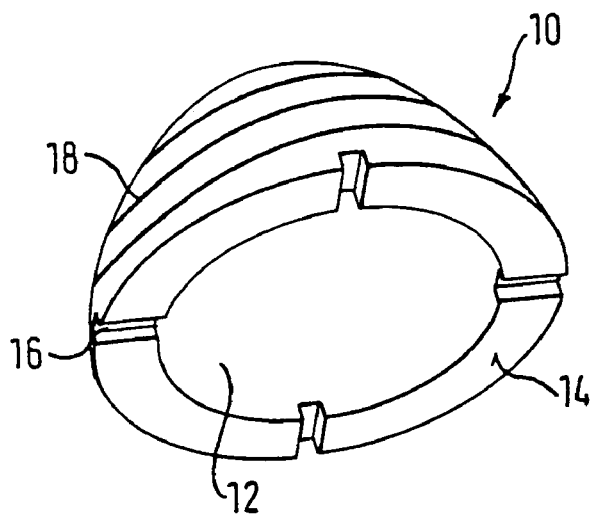

| | | |
|---|---|---|
| DE | 41 30 546 C2 | 3/1993 |
| DE | 92 12 420 U1 | 3/1994 |
| DE | 43 41 367 C1 | 6/1995 |
| DE | 44 34 539 C2 | 4/1996 |
| DE | 196 24 118 A1 | 12/1996 |
| DE | 195 43 110 A1 | 6/1997 |
| DE | 19543110 | 6/1997 |
| DE | 197 01 778 A1 | 6/1998 |
| DE | 197 51 284 A1 | 5/1999 |
| DE | 198 15 329 A1 | 10/1999 |
| DE | 199 52 550 A1 | 5/2001 |
| EP | 0 315 283 A3 | 5/1989 |
| EP | 0 328 478 A1 | 8/1989 |
| EP | 0 472 315 A1 | 2/1992 |
| EP | 0 574 098 A1 | 12/1993 |
| EP | 0 584 484 A1 | 3/1994 |
| EP | 0 834 294 A1 | 4/1998 |
| FR | 2 633 823 A1 | 1/1990 |
| GB | 2 093 701 A | 9/1982 |
| WO | WO 94/09722 | 5/1994 |
| WO | WO 95/32623 | 12/1995 |
| WO | WO 98/14128 | 4/1998 |
| WO | WO00/74741 | 12/2000 |

OTHER PUBLICATIONS

"Implantate zur Armierung der Huftpfanne" from Protek AG, Bern, 1971, no translation.

* cited by examiner

BONE IMPLANT

The present invention relates to a bone implant to support the fitting of an artificial socket into a damaged bone.

The loosening of artificial joints, in particular of artificial hip joints, is regularly associated with a loss of bone tissue in the patient. A specific form of this tissue loss is concentric osteolysis all around the normally semi-spherical, artificial acetabulum. The reconstruction of the bone defect is often very difficult and time-consuming, in particular when the bone defect at the rear of the acetabulum includes the inner corticalis. Currently, attempts are being made with great technical and time effort to bridge the bone defect by using metal implants in order to offer the replacement socket a stable support with a large area support at the healthy bone.

In this connection, the currently used methods use a combination of special metal implants and bone blocks, discs and granulate whose required size and quantity can only be determined during surgery. The operation is hereby substantially extended with all the disadvantages for the patient which result from this. Spacers are known from EP 0 834 294 A1 for prosthesis parts which can be cemented into bones and which consist of hardened bone cement.

In DE 195 43 110 1, a sterile bone matter for transplanting is known which is substantially free of fat, connective tissue and cartilage mass.

It is the object of the present invention to provide a bone implant with which the planning and operation time can be dramatically shortened in a replacement of damaged sockets.

This object is satisfied by a method having the features of claim 1.

In accordance with the invention, a standard product is provided which consists of spongeous bone, which maintains its biomechanical properties, is reworkable and can simultaneously serve for the anchoring of a socket. The base body can be inserted into the damaged bone, for example, by press fitting, in a short time, whereupon the socket of the endoprosthesis can be inserted into the cavity of the base body.

By using such a standardized intermediate part of natural spongiosa, which is inserted more or less as an "adapter", the planning and operation time can be substantially shortened since the carrying out of a plurality of individual measures to eliminate the bone defect and to anchor the joint shell can be dispensed with.

Advantageous embodiments of the invention are described by the description, the figures and the dependent claims.

It can also be advantageous to shape the base body with a structured surface at the outer side for a better fixing in place. It is, however, also possible to form the base body without a special outer structure and to anchor it by a press fitting or by cementing it in.

The bone implant is preferably produced from bovine bone.

The invention also relates to a set consisting of a plurality of bone implants of the said kind, with the bone implants in the set having different, standardized outer dimensions and wall strengths. In this connection, the inner diameters of the respective cavities are matched to the outer diameters of commercial artificial sockets. The planning and operation times can be even further shortened with such a set of bone implants since the surgeon already has bone implants with standardized sizes available which consist of preserved natural spongiosa.

The present invention further relates to a method for producing a bone implant for the installation of an artificial socket into a damaged bone in which a computer tomogram is made from the damaged body bone of the patient with the aid of which an artificial model of the damaged body bone is produced.

The producing of a model of a body bone with the aid of a computer tomogram is generally known.

It is a further object of the present invention to provide a method for the producing of a bone implant with which the planning and operation of a bone defect can be simplified.

The manufacture of the bone implant directly from the data of a computer tomogram is possible. The object can be solved in another way in a method of the kind initially named in that in the region of the bone defect a hardenable moldable mass is filled in at the model, in that the molding composition is shaped such that it forms a reception for an artificial socket, and in that a copy of the molded piece is made on a milling machine by scanning the hardened molded piece, said copy being milled from a piece of preserved spongiosa.

A bone implant gained in this way fits accurately into the bone defect and thus satisfies the demands of a stable, large-area support at the healthy bone. At the same time, possible defects in the rear wall of the acetabulum can be closed in a stable and reliable manner with this bone implant.

When forming a reception for a socket, the planned replacement acetabulum of an endoprosthesis, or a model thereof, can be inserted or pressed into the molding composition to form the outer contour of the socket or of the model in the molding composition.

It is also advantageous to provide means for fixing, i.e. to reproduce these in the molding composition. For this purpose, the most favorable direction of extent of securing elements such as screws or pins can be fixed by pressing pins into the molding composition. The desired or required length of these elements can likewise be fixed in advance. The securing elements then automatically fit correctly by pre-drilling the passages.

Figure 2:
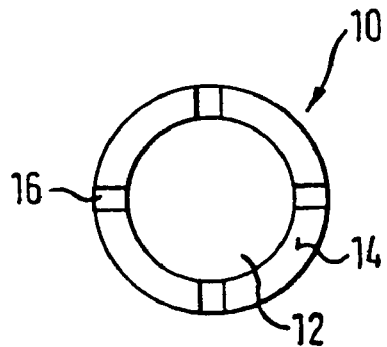
Figure 3:
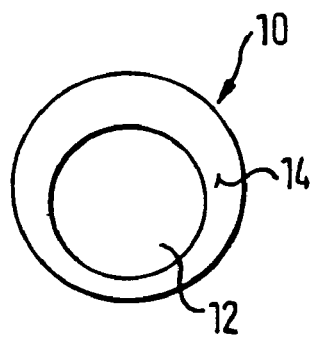

The present invention will described in the following by way of example with reference to advantageous embodiments and to the enclosed drawings. There are shown:

FIG. 1 a perspective view of a first embodiment of a bone implant;

FIG. 2 a plan view of the bone implant of FIG. 1;

FIG. 3 a plan view of a further embodiment of a bone implant; and

Figure 4:
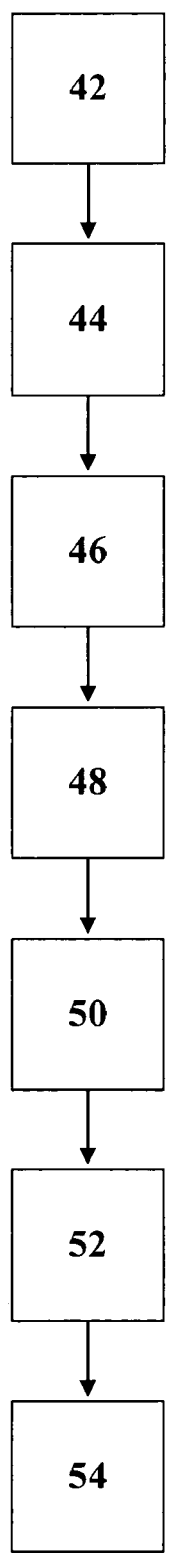

FIG. 4 is a schematic of an inventive method for manufacturing a bone implant.

The bone implant shown in FIG. 1 is an approximately semi-spherical shell 10 made of preserved, natural spongiosa which has a semi-spherical cavity 12. The outer contour of the bone implant 10 and the inner contour of the cavity 12 is thus semi-spherical or at least approximately semi-spherical. The circular aperture of the cavity 12 is surrounded by a peripheral end surface 14 which, in the example shown, has a plurality of radially extending recesses 16 to apply a setting tool.

An outer structure 18 is provided at the semi-spherical outer surface of the bone implant and the bone implant can be anchored in the damaged body with this in that a tool is inserted into the recess 16. The outer structure 18 can be formed as a thread.

FIG. 2 shows a plan view of the bone implant of FIG. 1. As can be recognized, the center of the aperture of the cavity 12 is arranged concentrically to the center of the base body 10.

In the embodiment shown in plan view in FIG. 3, the center of the cavity 12 is, in contrast, arranged offset to the center of the base body 10, i.e. the cavity 12 is arranged eccentrically. In this way, the position of the cavity can be varied by rotation. With this embodiment, which is anchored in the damaged bone by press fit, no outer thread is provided either. The recesses 16 are likewise omitted.

The outer diameters of the bone implants shown can vary in a range from approximately 30 mm to 70 mm. The inner diameters are each matched to commercial outer diameters of artificial joint shells of endoprostheses.

The present invention allows the preparation of the implant support with commercial bone rasps by rasping out the tissue-like structures down to the healthy bone. An implant is possible by press fitting by choosing the matching bone shell, with defects in the rear wall of the acetabulum being closed in a stable manner at the same time. The replacement acetabulum can now be fitted in the bone shell inserted into the damaged bone by press fitting, by cementing in or by screwing. A screw connection can also simultaneously serve for the anchoring of the bone shell in accordance with the invention.

The starting material for the bone implant in accordance with the invention is animal bone from animals of a sufficient size, preferably cows, but also from other animals of a similar size which can be kept under controlled conditions.

To remove the antigenicity, the bone is subjected to an osmotic treatment. Furthermore, an oxidizing treatment is carried out for denaturation of soluble proteins. To optimize virus deactivation, a reduction of pH to pH 3, or a treatment with caustic soda or another substance which destroys DNA/RNA, can take place. The dehydration takes place through organic solvents, preferably acetone. The concluding sterilization takes place through high-energy radiation, preferably γ rays with a maximum dose of 25 kGy. The bone treated in this manner maintains its natural mineral collagen bond and thus its bio-mechanical properties properties, and it can be reworked.

In a method for the manufacture of a bone implant for the replacement of damaged sockets, in accordance with the invention is depicted in FIG. 4 where a computer tomogram is first made from the damaged body bone of the patient with the aid of which an artificial model of the damaged body bone is produced 42. Subsequently, a hardenable molding composition is filled in in the region of the bone defect at the model 44, with the molding composition then being shaped such that it forms a reception for an artificial socket 46. Optionally, the socket of an endoprosthesis or a model of the socket is inserted into the molding composition to form the outer contour of the socket or of the model in the molding composition 48. In this connection, the surgeon fills a preferably self-hardening molding composition into the bone defect at the model and subsequently shapes the mass according to his wants. The artificial socket which should be inserted can be pressed into the molding composition at the desired point and thus be shaped. The fixing of the socket can likewise already be pre-planned.

Optionally, means are provided before the molding composition is hardened into a molded piece for later fixing of the bone implant to the damaged bone body 50.

Subsequently, the molding composition is allowed to set and a bone implant, which corresponds to the hardened formed piece 52, is produced by milling from a sufficiently large piece of preserved spongiosa of natural origin 54 (for example by copy milling) with the aid of the hardened formed piece. The copy of the molded piece is made on a milling machine by scanning the hardened molded piece. The implant gained in this way fits accurately into the defect and meets the demands on a stable, large-area support at the healthy bone. At the same time, possible background defects to the acetabulum can be closed in a stable and reliable manner with this bone implant.

What is claimed is:

1. A method for the manufacture of a bone implant for fitting an artificial socket into a damaged bone, in which a computer tomogram is made from the damaged body bone of the patient with the aid of which an artificial model of the damaged body bone is produced, wherein
   a) a hardenable molding composition is filled into the region of the bone defect at the model;
   b) the molding composition is shaped such that it forms a reception for an artificial socket;
   c) the molding composition is hardened into a molded piece; and
   d) a copy of the molded piece is made on a milling machine by scanning the hardenable molded piece, said copy being milled from a piece of preserved spongiosa.

2. A method in accordance with claim 1, characterized in that in step b) a socket of an endoprosthesis or a model of the socket is inserted into the molding composition to form the outer contour of the socket or of the model in the molding composition.

3. A method in accordance with claim 1, characterized in that, before step c), means are provided at the molding composition for the later fixing of the bone implant at the damaged body bone.

4. A bone implant comprising a piece of preserved spongiosa maintaining natural mineral collagen bond, the implant being formed by milling said piece of preserved spongiosa based on a molded piece derived from a computer tomogram.

5. The bone implant in accordance with claim 4 wherein the piece of spongiosa is formed to have a semicircular cavity.

* * * * *